United States Patent [19]

Landis

[11] Patent Number: 4,920,576
[45] Date of Patent: May 1, 1990

[54] VISOR-TYPE MASK FOR DENTISTS

[76] Inventor: Timothy J. Landis, 2006 McLaren Dr., Roseville, Calif. 95661-4945

[21] Appl. No.: 297,050

[22] Filed: Jan. 17, 1989

Related U.S. Application Data

[63] Continuation-in-part of Ser. No. 194,150, May 16, 1988, which is a continuation-in-part of Ser. No. 214,437, Jul. 1, 1988, which is a continuation-in-part of Ser. No. 229,349, Aug. 8, 1988.

[51] Int. Cl.⁵ .............................. A42B 1/06; A61F 9/06
[52] U.S. Cl. .................................................. 2/9; 2/10; 2/173; 2/185 R; 2/199; 2/200
[58] Field of Search .................... 2/9, 10, 173, 181.4, 2/185 R, 199, 200

[56] References Cited

U.S. PATENT DOCUMENTS

| | | | |
|---|---|---|---|
| 1,025,124 | 5/1912 | Corbett | 2/9 |
| 1,947,786 | 2/1934 | Lueck et al. | 2/173 |
| 1,955,232 | 4/1934 | Gallaway | 2/10 |
| 2,179,719 | 11/1939 | Goskey | 2/10 |
| 2,881,443 | 4/1959 | Barker Jr. | 2/9 |
| 2,978,709 | 4/1961 | Atha | 2/9 |
| 3,049,716 | 8/1962 | Stegeman | 2/12 X |
| 3,214,767 | 11/1965 | Weber | 2/9 |
| 3,475,766 | 11/1969 | Raschke | 2/9 |
| 3,705,760 | 12/1972 | Langendorfer et al. | 2/447 X |
| 4,055,857 | 11/1977 | Brucciani | 2/197 |
| 4,063,740 | 12/1977 | Mader | 2/185 X |
| 4,068,319 | 1/1978 | Wagenfeld | 2/197 |
| 4,335,471 | 6/1982 | Quigley Jr. et al. | 2/200 X |
| 4,345,336 | 8/1982 | Plastino | 2/187 |
| 4,625,341 | 12/1986 | Broersma | 2/9 X |
| 4,628,543 | 12/1986 | Hunt | 2/161 A X |
| 4,701,965 | 10/1987 | Landis | 2/9 X |

FOREIGN PATENT DOCUMENTS

| | | | |
|---|---|---|---|
| 3030451 | 2/1982 | Fed. Rep. of Germany | 2/426 |
| 14855 | 9/1916 | United Kingdom | 2/10 |
| 176643 | 3/1922 | United Kingdom | 2/10 |
| 234022 | 5/1925 | United Kingdom | 2/10 |

*Primary Examiner*—Werner H. Schroeder
*Assistant Examiner*—Jeanette E. Chapman
*Attorney, Agent, or Firm*—Julian Caplan

[57] ABSTRACT

An improvement upon other inventions of Applicant wherein a visor which is attached to the head of the user supports a shield which hangs in front of the face of the wearer, protecting the eyes, nose and mouth from contamination which might be carried by dental and medical patients or in other environments. This invention differs in that the support of the shield is accomplished by forward extending tabs on the forward edge of the visor projecting into slots formed near the upper edge of the shield.

14 Claims, 7 Drawing Sheets

VISOR-TYPE MASK FOR DENTISTS

CROSS-REFERENCE TO RELATED APPLICATIONS

This application is a continuation-in-part of Applicant's co-pending applications Ser. No. 194,150 filed May 16, 1988, 214,437 filed Jul. 1, 1988, and 229,349 filed Aug. 8, 1988. This application is also an improvement upon Ser. No. 229,448 filed Aug. 8, 1988 in which Applicant is a co-inventor. Reference is further made to Applicant's U.S. Pat. No. 4,701,965, on which the present application is an improvement.

BACKGROUND OF THE INVENTION

1. Field of the Invention

This invention relates to a new and improved visor-type mask for dentists, surgeons and others to avoid contamination with germs and viruses of their patients and customers. A visor, which may be held on the head by various means hereinafter described, supports a transparent plastic shield of sheet plastic extending down below the mouth of the wearer and around the sides of the head, thus providing superior frontal and lateral protection from splashing and spattering with bodily fluids. The present invention differs from the patent and applications mentioned in the preceding paragraph in that tabs project from the forward edge of the visor and fit through slots spaced downward from the upper edge of the shield, thereby supporting the shield.

2. Description of Related Art

Surgical masks of gauze and paper have been used to prevent intercontamination of doctor and patient. However, wearing such masks is hot and uncomfortable and, frequently, frightening to patients. Putting the masks on and removing them are time-consuming and sometimes difficult. Breath condenses within the mask and hence the latter becomes saturated with moisture and thereby fails to be an effective barrier to viruses and bacteria.

Applicant and others have marketing masks consisting of a visor which projects forward from the forehead and is held in place by various means, extending around the sides and frequently the back of the head. One typical such device is shown in U.S. Pat. No. 4,701,965. The present invention differs from these prior art devices in two respects: first, the means of attachment to the head is novel, as is disclosed in the aforesaid co-pending applications. Second, instead of tabs on the upper edge of the shield fitting into slots adjacent the front edge of the visor, the projecting tabs are formed on the forward edge of the visor and fit into slots formed near the upper edge of the shield.

The present invention is particularly suited to surgical use in that it may be sterilized (as by ethylene dioxide gas) before and between uses and may be discarded after a single use, if desired. Surgeons find use of the device comfortable even during prolonged operations, since localized pressure on the head does not occur and, further, the device is very lightweight.

SUMMARY OF THE INVENTION

A visor which projects forward from the forehead of the wearer is mounted on the head by various means such as straps fitting around the sides of the head which are fastened together at the back of the head by means of snaps, Velcro material, and buckles of various types, an elastic member which is attached to the ends of short straps, by making the strap which fits around the back of the head integral with the visor and formed of a stretchable material such as sponge rubber, by means of a surgeon's cap to which the visor is attached, or the like. A shield of transparent flexible plastic material is attached to the visor and hangs down over the eyes, nose and mouth and around the sides of the face. The visor has projections spaced around its forward edge and the shield has complementary slots dimensioned so that the projections or tabs snap therethrough. In one form of the invention, the visor and shield are hingedly connected. With the visor mounted on the head and the shield suspended therefrom, the user is protected from contamination by germs or viruses of a patient or customer. Otherwise, blood or dental detritus and body fluids might otherwise contact the eyes, nose or mouth of the user.

Other objects of the present invention will become apparent upon reading the following specification and referring to the accompanying drawings in which similar characters of reference represent corresponding parts in each of the several views.

DESCRIPTION OF PREFERRED EMBODIMENTS

Figure 12:
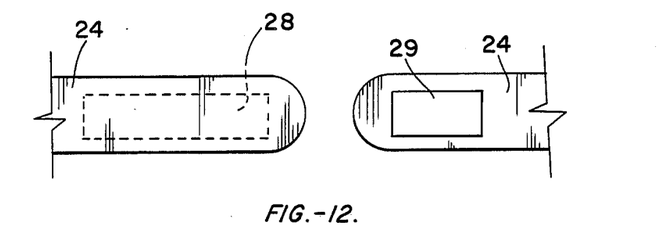
FIGS. 12–14 are enlarged fragmentary views showing the extremities of bands or straps used to connect the bands or straps together and illustrating modified means for fastening the same.
Figure 13:
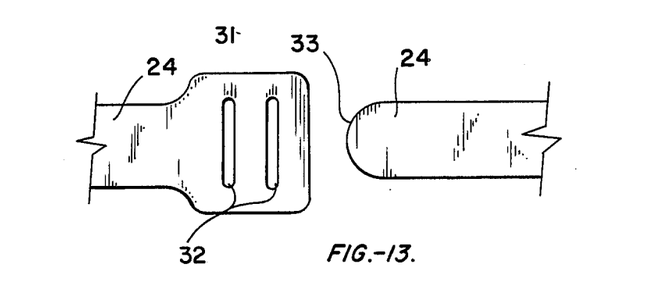
Figure 14:
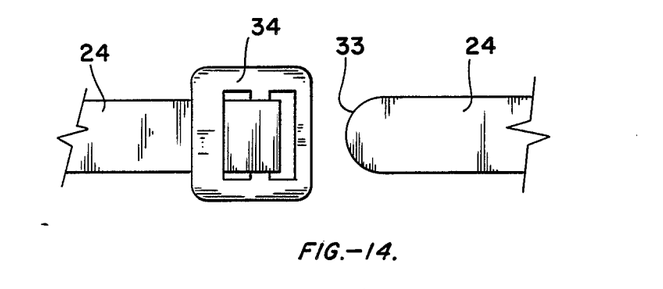

Directing attention to the modification shown in FIGS. 1–4, visor 21 has an inner edge 22 shaped to engage the forehead of the wearer and an outward projecting outer edge 23. Straps 24 extend rearwardly of visor 21 and are of a length to extend around the head of the wearer. Male snap fasteners 26 are attached near the extremity of one band 24 and female snap fasteners 27 to the opposite strap. As shown, there are two fastener elements 26 and four fastener elements 27 to give wide adjustability, but it will be understood that the number of fastener elements is subject to considerable modification. The visor 21 may be made of a thin, flexible transparent plastic material or of any other suitable material. Directing attention to the modification of FIG. 12, Velcro-like materials 28 and 29 may be attached (as by cement or glue) adjacent the extremities of straps 24. FIG. 13 shows a further modification wherein an enlarged end 31 is formed on one strap 24 and transverse slots 32 formed therein. The rounded end 23 of the other strap 24 may penetrate the slots 32 so that the two straps are buckled together. FIG. 14 shows still another modification wherein buckle 34 of any suitable form is attached to the end of one strap 24, the rounded end 33 of the opposite strap engaging the buckle 34 in the manner of belt buckles and the like. It will be understood that a wide variety of other means for attaching the straps 24 together may be employed.

Projecting forwardly from outer edge 23 are a plurality of tabs 36. The shape of tabs 36 is subject to variation. In the preferred form shown in FIG. 1, the outer edge 37 is straight and there are inwardly curved arcuate side edges 38 on either side.

Figure 1:
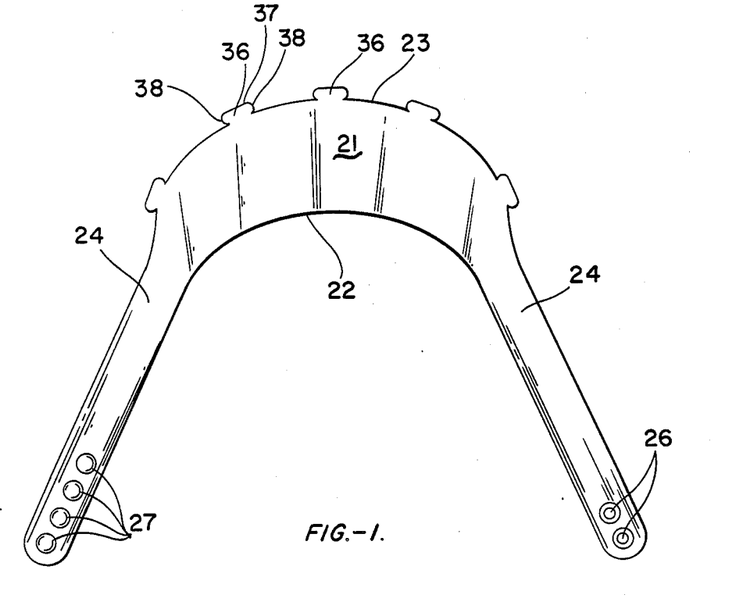
FIG. 1 is a plan view of a visor in accordance with the present invention.
Figure 2:
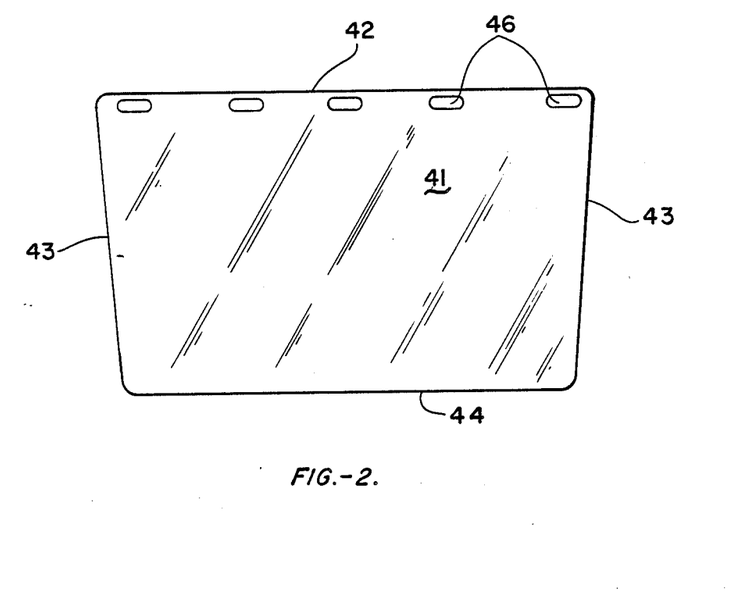
FIG. 2 is a plan view of a shield laid flat.
Figure 3:
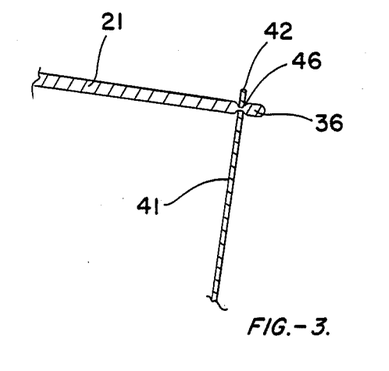
FIG. 3 is an enlarged fragmentary sectional view showing how the tab of the visor projects through a slit in the shield.
Figure 4:
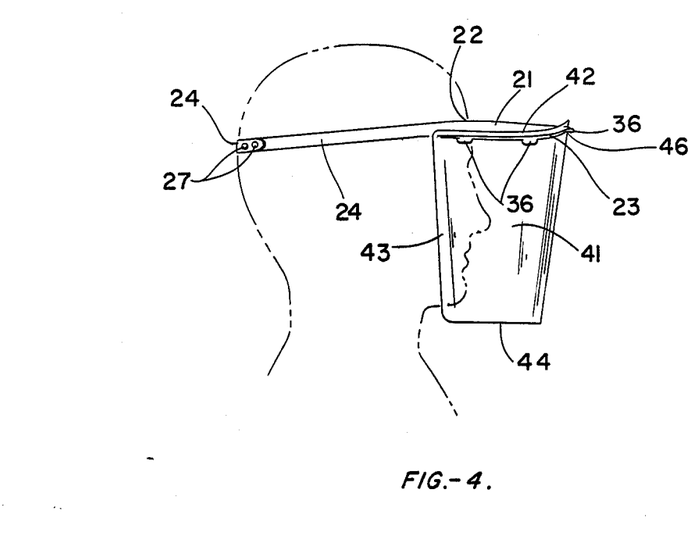
FIG. 4 is a perspective view showing the shield assembled on the visor mounted on the head of the wearer.

Shield 41 is preferably formed of a transparent, flexible plastic material. It will be understood that part or all of the shield 41 may be provided with a filter to filter bright lights or ultraviolet lights used in dentistry and surgery. Shield 41 has an upper edge 42, downward converging side edges 43 and a bottom edge 44. Slots 46 are formed near the top edge 42 to receive the projections 36. The shape of slots 46 is such that the tabs 36 may be pushed through and the sides 38 of the projections 36 hold the projections 36 in place. By reason of the curved shape of outer edge 23, shield 41 assumes a curved shape best shown in FIG. 4, with the sides 43 extending around the sides of the face and the shield protecting the eyes, nose and mouth of the user.

Figure 5:
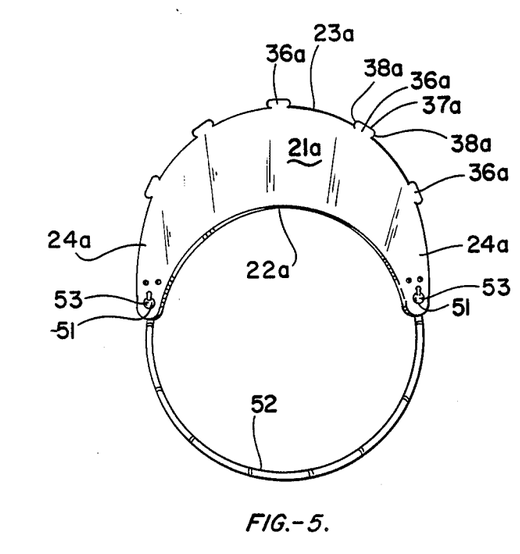
FIG. 5 is a view similar to FIG. 1 of a modification.

Directing attention now to the form of invention shown in FIG. 5, the straps 24a are shorter than those of the preceding modification. Holes 51 are formed adjacent the extremities of the straps 24a. An elastic band 52, such as a piece of rubber tubing, is threaded through the holes 51 and may be held in place by various attachment means such as inserting a ball 53 in the ends of the tubing to expand the dimensions thereof and to prevent the ends of the elastic band 52 from escaping from the holes 51.

Figure 6:
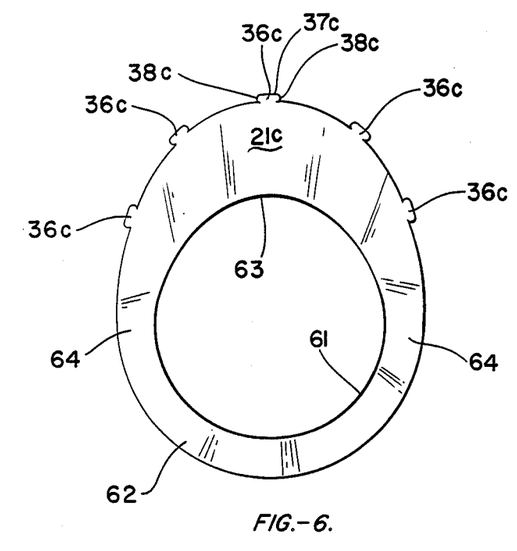
FIG. 6 is a plan view of a further modified visor wherein the visor is formed integral with a strap which attaches it to the head.

In the modification of FIG. 6, visor 21c is formed from a single piece of stretchable material such as sponge rubber or a stretchable plastic. One or both surfaces of the visor 21c may be ornamented by cloth or other material adhered thereto. An ellipsoidal hole 61 is cut in the visor 21c so that a single band 62 fits behind the head of the wearer, the sides fitting around the sides of the head. Thus the front edge 63 engages the forehead of the wearer as does the inner edge 22 of the visor 21, shown in FIG. 1. After the shield has been attached to the visor 21c, the band 62, 64 is pulled down over the head, fitting around the sides and back of the head.

Figure 7:
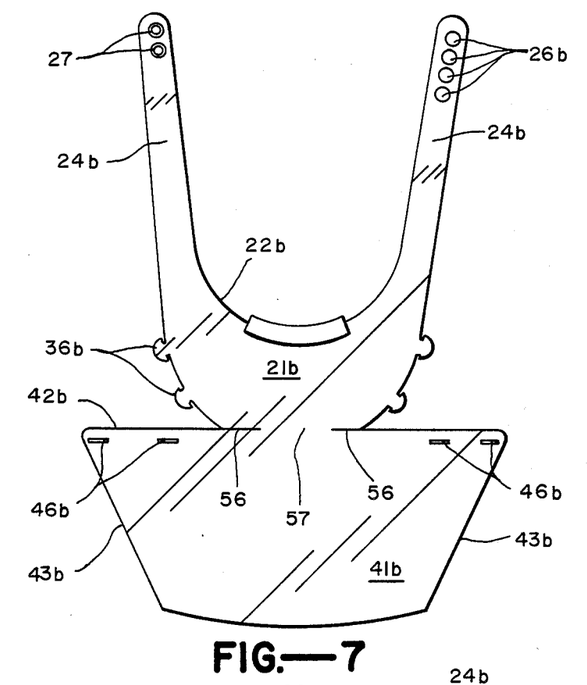
FIG. 7 is a plan view of a further modification wherein the visor, attachment means and shield are formed from an integral blank.
Figure 8:
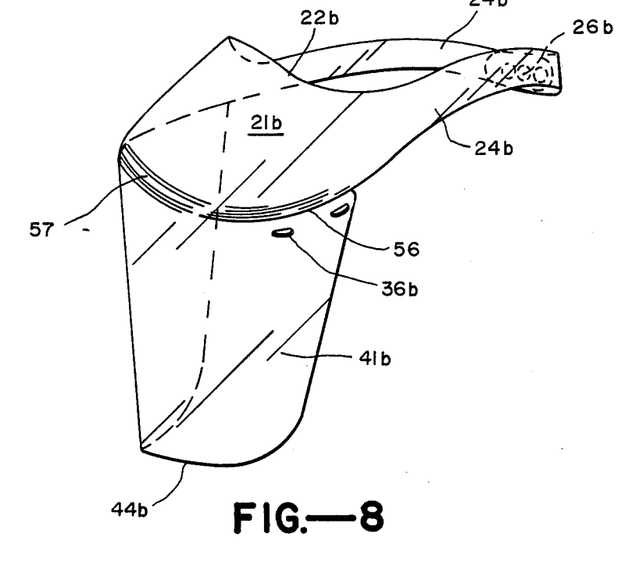
FIG. 8 is a perspective view showing a modification of FIG. 7 in position of use.

In the modification of FIG. 7, the visor 21b and shield 41b are formed integral. Thus, slits 56 are formed extending inward from the upper edge 42b of visor 41b, extending toward but terminating short of the middle. Thus there is an uncut hinge portion 57 inward of slits 56. Slots 46b (here shown as two in number on each side of hinged area 57 receive complementary tabs 36b projecting from outer edge 23b of visor 21b. Although the same means for attaching the ends of the bands 24b is illustrated in FIGS. 7 and 8 as in FIG. 1, it will be understood that various means may be used to support the visor 21b from the head, including the means shown in FIGS. 9-11 hereinafter explained. In use, the bands 24b are brought around the sides of the head and connected together at the back. The shield 21b is bent down so that it extends vertically, as best shown in FIG. 8.

Figure 9:
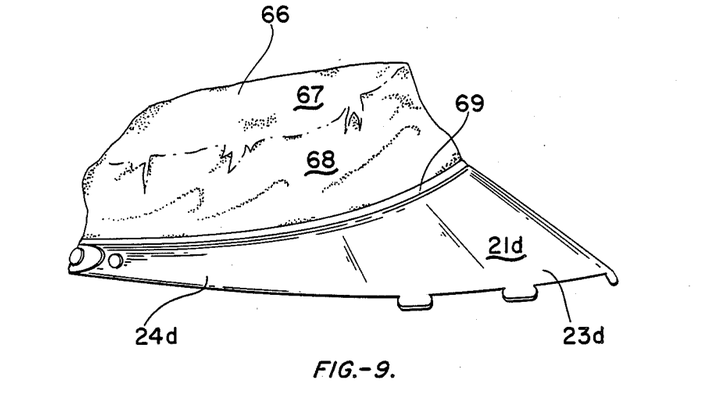
FIG. 9 is a perspective view of a further modified visor attached to a surgeon's cap.
Figure 10:
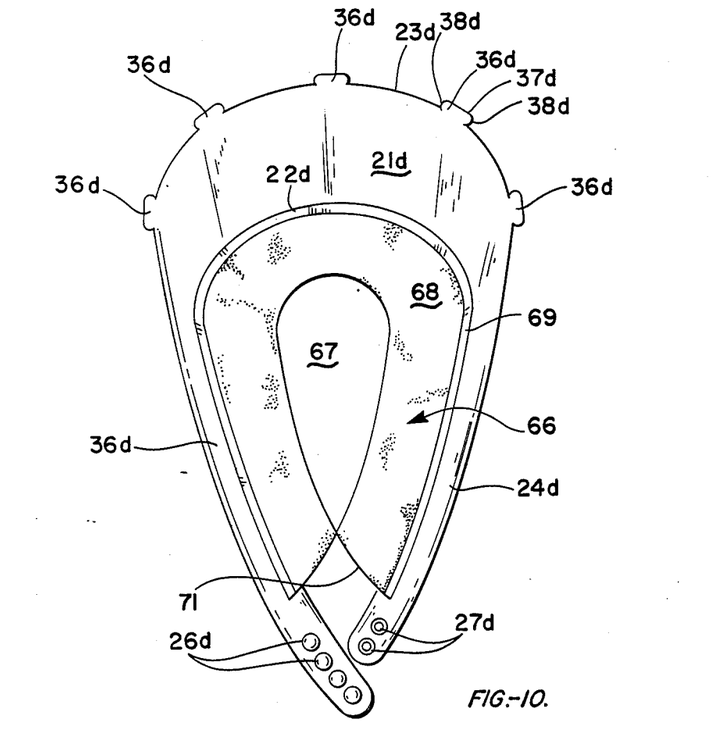
FIG. 10 is a top plan view of a modification of FIG. 9 prior to the straps being snapped together.

In FIG. 9, the visor 21d is attached to a surgeon's or surgical nurse's cap 66. Such caps are of varying shape. As shown in FIGS. 9 and 10, the cap has a crown 67 from which depend sides 68. Reinforcing tape or other reinforcing means is stitched or otherwise adhered to the lower edge of the sides 68 and the reinforcement 69 is attached to the visor 21d. Notch 71 is formed at the back of the cap and this notch is closed over when the ends of the straps 24d are connected together as by the snap fasteners 26d, 27d. It will further be understood that various other means may be used to secure the bands 24d together, many of which have been heretofore described.

Figure 11:
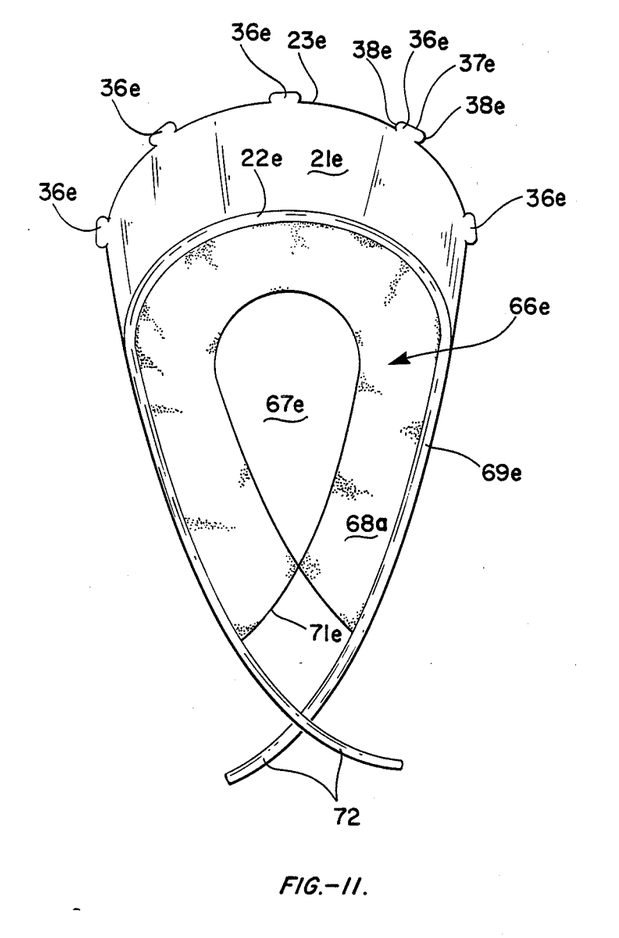
FIG. 11 is a view similar to FIG. 10 of a further modification.

The modification of FIG. 11 shows still another means for securing the surgical cap 66e to the head of the wearer. Thus the reinforcements 69 are extended into ties 72 projecting beyond the ends of the visor. These ties are knotted together behind the head to hold the cap 66e in place. Shields similar or identical to that shown in FIG. 2 may be used with the visors of FIGS. 5, 6, 9 and 11.

It will be understood that in many of the modifications herein illustrated, elements of the visor are substantially identical to those in other modifications and the same reference numerals followed by the subscripts a, b, c, d, and e are used to designate corresponding parts in the modifications of FIGS. 5, 7, 6, 9 and 11, respectively.

What is claimed is:

1. A face mask comprising a visor, said visor comprising first means comprising a bill for engaging or lying against the forehead, said bill projecting forwardly above eye level and second means for attaching the visor to the head of the wearer, said bill being formed with first cooperating means extending along the outer edge of said bill, said first cooperating means comprising a plurality of projections spaced along said outer edge of said bill, and a shield transparent over at least a substantial portion of its area, said shield having an upper edge, second cooperating means on said shield shaped and positioned to engage said first cooperating means so that said shield is supported by said visor, said shield being dimensioned to extend down below the mouth and around the face, said second cooperating means comprising spaced slits in said shield dimensioned to receive and retain said projections, said shield having its upper edge disposed above said bill and being further disposed in contact with said outer edge of said bill.

2. A mask according to claim 1 in which said visor is initially formed of a flat sheet of material which is bendable to assume a visor shape when said second means is brought around the back of the head.

3. A mask according to claim 2 in which said second means comprises a first and a second narrow tail, said tails having cooperating fastening means to adjustably fit around the head.

4. A mask according to claim 1 in which said second means comprises a member formed of a length of elastic material dimensioned to fit behind the head of the wearer and having attachment means on each end engageable with said first means.

5. A mask according to claim 1 in which said projections are dovetail, having a maximum width greater than the length of said slits when said visor is unstressed.

6. A mask according to claim 5 in which the outer edges of said projections are rounded.

7. A mask according to claim 1 in which said second means is formed by a hole in said visor, said visor being of a continuous piece of material having an integral narrow band around one end of said hole adapted to fit around the back of the head of the wearer, said visor having said bill on the side of said hole opposite said band.

8. A face mask for surgeons and surgical personnel according to claim 1 in which said second means comprises a disposable surgeon's cap having head covering means terminating in a lower edge, and means for attaching said lower edge to said bill.

9. A mask according to claim 8 in which said cap is made of a paper-like substance and has a crown and sides around said crown.

10. A mask according to claim 8 in which said cap is formed with a reinforcing binding along said lower edge, said binding extending rearward to form ties, said ties comprising said second means.

11. A device according to claim 1 in which said visor is of a sponge rubber-like material and said projections are wider at their outer ends than their inner ends, whereby when said projections are forced through said slits said projections deform and then return to original shape to retain said shield suspended from said visor.

12. A mask according to claim 1 in which said visor and said shield comprise a unitary blank of thin, transparent material,
    said bill having a curved inner edge to conform to the shape of the forehead of the wearer and a curved outer edge, a hinge section on said outer edge, said hinge section being hingedly connected to said upper edge of said shield,
    said first and second cooperating means being cooperable to be engaged to cause the top edge of said shield to conform substantially to the shape of said outer edge.

13. A device according to claim 12 in which said upper edge is substantially straight and said blank is formed with cuts extending inward and constituting extensions of said top edge, the inner ends of said cuts being spaced apart by said hinge section.

14. A device according to claim 12 which further comprises a protective pad on said inner edge and means securing said pad to said spacer portion.

* * * * *